(12) United States Patent
Axelrod et al.

(10) Patent No.: US 7,449,758 B2
(45) Date of Patent: Nov. 11, 2008

(54) POLYMERIC PIEZORESISTIVE SENSORS

(75) Inventors: Blake W. Axelrod, Pasadena, CA (US); Michael L. Roukes, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 473 days.

(21) Appl. No.: 11/205,318

(22) Filed: Aug. 17, 2005

(65) Prior Publication Data

US 2006/0071286 A1      Apr. 6, 2006

Related U.S. Application Data

(60) Provisional application No. 60/602,113, filed on Aug. 17, 2004, provisional application No. 60/602,099, filed on Aug. 17, 2004.

(51) Int. Cl.
*H01L 29/84* (2006.01)
(52) U.S. Cl. ............................... 257/415; 257/E51.046; 374/46
(58) Field of Classification Search .................... 374/46; 257/414, 415, E51.002, E51.019, E51.021, 257/E51.046; 438/52, 99
See application file for complete search history.

(56) References Cited

U.S. PATENT DOCUMENTS

| | | | |
|---|---|---|---|
| 5,427,841 A | | 6/1995 | De Leeuw et al. |
| 5,447,824 A | | 9/1995 | Mutsaers et al. |
| 5,620,800 A | | 4/1997 | De Leeuw et al. |
| 6,143,206 A | * | 11/2000 | Handa et al. ................. 252/500 |
| 6,294,401 B1 | * | 9/2001 | Jacobson et al. ............. 438/99 |
| 6,429,450 B1 | | 8/2002 | Mutsaers et al. |
| 6,593,731 B1 | | 7/2003 | Roukes et al. |
| 6,635,406 B1 | | 10/2003 | De Leeuw et al. |
| 7,256,467 B2 | * | 8/2007 | Reid et al. ................... 257/415 |
| 7,270,205 B2 | | 9/2007 | Sakai et al. |
| 7,302,856 B2 | | 12/2007 | Tang et al. |
| 2005/0104621 A1 | * | 5/2005 | Kawahara et al. ............. 326/39 |
| 2006/0205109 A1 | * | 9/2006 | Cox et al. ..................... 438/99 |

FOREIGN PATENT DOCUMENTS

WO    WO 2004/041998 A2    5/2004

OTHER PUBLICATIONS

Afzali et al., "Photosensitive Pentacene Precursor: Synthesis, Photothermal Patterning, and Application in Thin-Film Transistors," Adv. Mater., Dec. 17, 2003, 15(24): 2066-2069.

Chou et al., "A microfabricated device for sizing and sorting DNA molecules," Proc. Natl. Acad. Sci. USA, Jan. 1999, 96:11-13.

Dembo et al., "Stresses at the Cell-to-Substrate Interface during Locomotion of Fibroblasts," Biophysical Journal, Apr. 1999, 76:2307-2316.

Drury et al., "Low-cost all-polymer integrated circuits," Appl. Phys. Lett., Jul. 6, 1998, 73(1):108-110.

(Continued)

*Primary Examiner*—W. David Coleman
(74) *Attorney, Agent, or Firm*—Foley & Lardner LLP

(57) ABSTRACT

A MEMS system, such as a biosensor, includes a micromechanical resonator and a piezoresistive sensing element which includes an organic semiconductor, such as an organic thin film transistor.

18 Claims, 5 Drawing Sheets

OTHER PUBLICATIONS

Gelinck et al., "High-preformance all-polymer integrated circuits," Appl. Phys. Lett., Sep. 4, 2000, 77(10):1487-1489.

Gelinck et al., "Flexible active-matrix displays and shift registers based on solution-processed organic transistors," Nature Materials, Feb. 2004, 3:106-110.

Gundlach et al., "Pentacene Organic Thin-Film Transistors—Molecular Ordering and Mobility," IEEE Electron Device Letters, Mar. 1997, 18(3):87-89.

Janmey, Paul A., "The Cytoskeleton and Cell Signaling: Component Localization and Mechanical Coupling," Physiological Reviews, Jul. 1998, 78(3):763-781.

Maniotis et al., "Demonstration of mechanical connections between integrins, cytoskeletal filaments, and nucleoplasm that stabilize nuclear structure," Proc. Natl. Acad. Sci. USA, Feb. 1997, 97:849-854.

Meijer, E.J., "The Meyer-Neldel rule in organic thin-film transistors," Appl. Phys. Lett., Jun. 5, 2000, 76(23):3433-3435.

Meijer et al., "Solution-processes ambipolar organic field-effect transistors and inverters," Nature Materials, Oct. 2003, 2:678-682.

Munevar et al., "Traction Force Microscopy of Migrating Normal and H-ras Transformed 3T3 Fibroblasts," Biophysical Journal, Apr. 2001, 80:1744-1757.

Qiu et al., " Preparation and characteristics of flexible all-organic thin-film field-effect transistor," Chinese Science Bulletin, 2003, 48(15):1554-1557.

Tan et al., "Cells lying on a bed of microneedles: An approach to isolate mechanical force," PNAS, Feb. 18, 2003, 100(4):1484-1489.

Touwslager et al., "I-Line lithography of poly-(3,4-ethylenedioxythiophene) electrodes and application inall-polymer integrated circuits," Appl. Phys. Lett., Dec. 9, 2002, 81(24):4556-4558.

Unger et al., "Monolithic Microfabricated Valves and Pumps by Multilayer Soft Lithography," Science, Apr. 7, 2000, 288:113-116.

* cited by examiner material reference:

POLYMERIC PIEZORESISTIVE SENSORS

CROSS-REFERENCE TO RELATED PATENT APPLICATIONS

This application claims benefit of priority of U.S. Provisional Application Ser. No. 60/602,113, filed on Aug. 17, 2004, and U.S. Provisional Application Ser. No. 60/602,099, filed on Aug. 17, 2004. All of the above mentioned applications are incorporated herein by reference in their entirety.

BACKGROUND OF THE INVENTION

This invention is related specifically to piezoresitive sensors for microelectromechanical systems (MEMS), and specifically to organic semiconductor piezoresistive sensors.

Microelectromechanical systems (MEMS) include devices with features having a size less than 100 microns in at least one dimension, and preferably in two or three dimensions. Preferably, these features comprise movable features or elements, such as cantilevers, diaphragms, clamped beams, wires, etc. Microelectromechanical systems include, but are not limited to, scanning probe microscopes (SPM), such as atomic force microscopes (AFM), force and pressure sensors, flow sensors, chemical and biological sensors, and inertial sensors, such as accelerometers and motion transducers. For example, chemical and biological sensors may comprise one or more cantilevers having a surface coated with a material which selectively binds to a chemical or biological analyte (i.e., gas or liquid analyte containing or consisting of the chemical or biological species of interest).

Piezoresitive displacement detection techniques are attractive in MEMS because they are able to be fully integrated and are easy to use. Most of these applications use p-type doped silicon layer as the piezoresistive sensing element.

Silicon has traditionally been used as a piezoresistive strain sensor due to its high piezoresistance coefficients and thus high sensitivity. However, silicon is very stiff, with a Young's modulus of $10^{11}$ Pa which reduces sensitivity. Piezoresistance in gold wires integrated into Su8 structures have been utilized in order to take advantage of the lower Young's moduli in gold and Su8. However, the piezoresistance coefficients in gold are small compared to those of silicon.

One application of sensors is for the coupling to a single cell for measuring forces exerted by the cell on its surroundings, thereby probing the structural state of the cell cytoskeleton. It is known that the structural state of the cytoskeleton is inseparably linked to the functional status of the cell. Early measurements probing the cytoskeleton have been made with micromanipulated microbeads, micropipettes and microfabricated post-array-detectors. These measurements are limited in spatial resolution (down to approximately 10 microns), force resolution (down to approximately 10 nanonewtons) and time resolution (only single shot measurements were possible).

Traction force microscopy, a more recent technique, observes the displacement of fluorescent beads suspended in a polyacrylamide membrane while a cell migrates across the membrane. Traction force microscopy achieves improved spatial resolution (down to approximately 3-4 microns), force resolution (down to approximately 500 piconewtons) and time resolution (down to approximately 40 seconds). However, the system requires unobstructed optical access to the membrane which prevents integration of force actuators and microfluidics.

SUMMARY OF THE INVENTION

A MEMS system, such as a biosensor, includes a micromechanical resonator and a piezoresistive sensing element which includes an organic semiconductor, such as an organic thin film transistor

DETAILED DESCRIPTION OF THE INVENTION

Organic Semiconductors

Figure 1A:
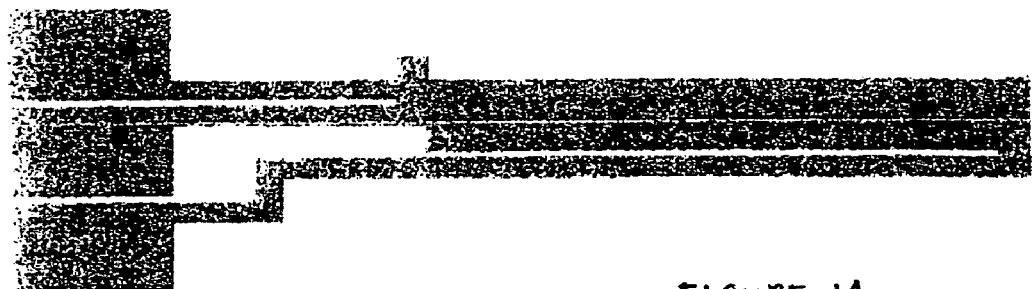
FIG. 1A shows a top view of a sensing cantilever of a first embodiment of the present invention.

Organic semiconductors, such as pentacene, are excellent candidates for strain and force sensors with low Young's moduli. Charge transport in organic semiconductors is believed to be due to hopping conduction of polarons and is limited by thermal hopping between individual molecules in amorphous films and single crystal grains in polycrystalline films. The thermal hopping mobility varies exponentially with the barrier height between sites. Thus, a tensile or compressive strain which is sufficient to affect the barrier height is measured by observing the resulting change in mobility in the film.

Pentacene channels in thin film transistors have been found to show increased mobility under compressive strains and decreased mobility under tensile strains while analyzing pentacene transistors for flexible displays. In pentacene, the strain dependent mobility is likely due to a change in hopping distance between single crystal grains in the polycrystalline pentacene. As a result, pentacene channels in thin film transistors are able to be used as piezoresistance based force and strain sensors. In Qiu Yong et al. (Chi. Sci. Bul. 48, 1554-1557 (2003)), the data presented indicates that pentacene's longitudinal piezoresistance coefficient is between 10 and 100, which is similar to that of silicon. Most organic materials, such as pentacene, have a Young's moduli in the range of $10^5$ Pa to $10^9$ Pa. Consequently, combining the effects of a low Young's moduli with the high piezoresistance coefficients of organic semiconductors, sensors such as force and strain sensors utilizing such organic semiconductors will make especially sensitive force and strain sensors.

Thus, in MEMS where high sensitivity is desirable, the piezoresistive effect is observed in organic semiconductors which function as channels of thin film transistors. MEMS include devices with features having a size of less than 100 microns, such as less than 10 microns in at least one dimension, and preferably in two or three dimensions. Preferably, these features comprise movable features or elements, such as cantilevers, diaphragms, clamped beams, wires, etc. Microelectromechanical systems include, but are not limited to, scanning probe microscopes (SPM), such as atomic force microscopes (AFM), force and pressure sensors, flow sensors, chemical and biological sensors, and inertial sensors, such as accelerometers and motion transducers. For example, chemical and biological sensors may comprise one or more cantilevers having a surface coated with a material which selectively binds to a chemical or biological analyte (i.e., gas or liquid analyte containing or consisting of the chemical or biological species of interest).

The thin film transistor is applied to a movable element within the MEMS. The movable element is preferably resilient, such as a mechanical resonator. Known mechanical resonators used in microelectromechanical sensors and scanning probe microscopes include torsional resonators, force sensing beams, cantilevers and membranes such as diaphragms. For example, the resonator preferably comprises a micron sized cantilever. However, it should be understood that the invention can be used with other resonators, including, but not limited to, doubly clamped beams, torsional resonators, and diaphragm resonators. Non-limiting examples of doubly clamped beam resonators, torsional resonators and diaphragm resonators are disclosed in U.S. patent application Ser. No. 10/826,007, U.S. Pat. No. 6,593,731 and PCT Application PCT/US03/14566 (published as WO/2004/041998) and its counterpart U.S. patent application Ser. No. 10/502,641, all incorporated herein by reference in their entirety. For example, a doubly clamped beam resonator comprises a beam that is fixed on both ends, but whose middle portion is free hanging so that it can flex or move perpendicular to its length. A torsional resonator may comprise, in a non-limiting example, a flexible diamond or polygonal shaped structure mounted at two anchor points and which can move by twisting or turning about an axis between the anchor points, as described and illustrated in U.S. Pat. No. 6,593,731. A diaphragm resonator may comprise any plate shaped resonator which is anchored at one or more edges and whose middle portion is free hanging so that it can move or flex in one or more directions. An example of a diaphragm resonator is a trampoline resonator. The sensors may comprise static or dynamic sensors which measure static movement or deflection of the resonator or a change in dynamic movement or deflection of the resonator, respectively, in response to a detectable stimulus or analyte.

Two exemplary embodiments of how organic semiconductors, in particular pentacene, are used as the piezoresistive sensing element in MEMS are described below.

First Embodiment

In a first embodiment, a sensor comprising a thin film transistor sensing element 10 and a resonator 12 is described. However, it should be noted that a scanning probe microscope (SPM) tip, such as atomic force microscopes (AFM) tip may also have a similar configuration. The micromechanical resonator 12 is in the form of a simple force sensing cantilever (i.e., a microcantilever having a thickness of 10 microns or less). The cantilever 12 preferably comprises a polymer cantilever, such as a parylene cantilever. Other organic polymer materials such as Su8 may also be used. Inorganic materials such as semiconductors (e.g. silicon (Si) and gallium arsenide (GaAs)) and insulators (e.g. silicon dioxide ($SiO_2$) and silicon nitride ($Si_3N_4$)) may also be used as cantilever materials.

The thin film transistor 10 preferably comprises an all organic thin film transistor which is located on a cantilever 12. The transistor 10 functions as the piezoresistive sensing element for the cantilever and is located on the cantilever. The thin film transistor 10 comprises is made up of a first layer of conducting organic polymer, such as polyaniline or poly(3,4-ethylenedioxythiophene) (PEDOT), that acts as a gate electrode 14, and a second layer of organic semiconductor 16, such as pentacene, that acts as the channel of the transistor 10. Two electrodes made of a conducting organic polymer such as polyaniline or poly(3,4-ethylenedioxythiophene) (PEDOT), act as the source and drain electrodes 18, are located on the organic semiconductor 16. The source and drain electrodes 18, as well as the gate electrode 14, may alternatively be made of other conductive materials, such as metal or polysilicon.

Figure 1B:
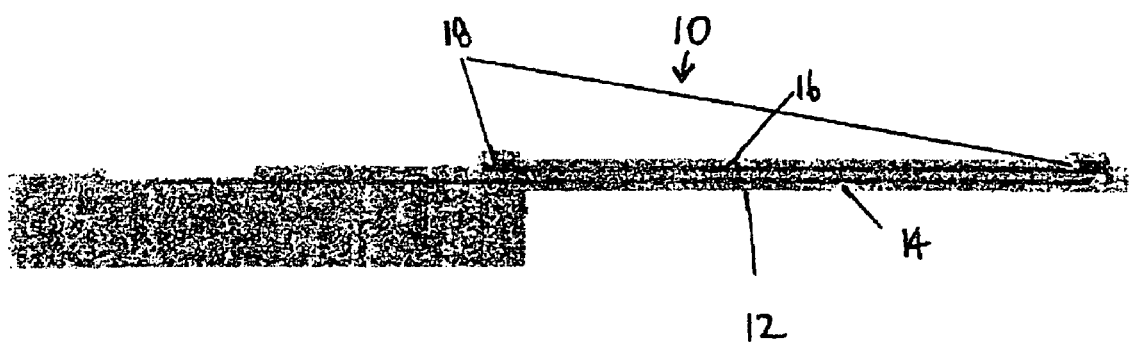
FIG. 1B shows a cross-sectional view of the cantilever of the first embodiment of FIG. 1A.

FIG. 1B shows a bottom gate thin film transistor. However, the thin film transistor may be a top gate thin film transistor. The thin film transistor may be a co-planar transistor (i.e. with the source and drain electrodes and the gate electrode on the same side of the channel), or a staggered thin film transistor (i.e. with the source and drain electrodes on opposite sides of the channel).

During operation of the force sensing cantilever, the gate electrode 14 is biased in order to accumulate charge in the organic semiconductor channel layer 16. Due to the piezoresistive effect of the organic semiconductor 16, any strain in the organic semiconductor 16 due to any force or strain applied to the cantilever 12 is measured by measuring the source-drain current between the source and drain electrodes 18 for a given bias on the gate electrode 14. Preferably, the change is current is measured in response to the applied strain or force.

Second Embodiment

In a sensor of a second embodiment, an organic semiconductor, such as pentacene, is similarly employed as the channel of a thin film transistor, and applied on a mechanical resonator in the form of a membrane or a diaphragm, in a MEMS sensor. In this embodiment, instead of a single sensor, a dense array of sensors is fully integrated on the surface of a compliant membrane. The array of sensors comprises individually addressable, accumulation mode, p-type, thin film transistors, with each thin film transistor functioning as a sensing element. Thus, the sensor array contains one resonator membrane and a plurality of sensing elements. The thin film transistor is preferably fabricated entirely from organic materials as in the first embodiment. The array of sensors is supported on a suspended elastomer membrane, preferably made entirely of an organic material. The high compliance of the elastomer membrane and the preferred all organic materials fabrication will enable improved force resolution.

Figure 2A:
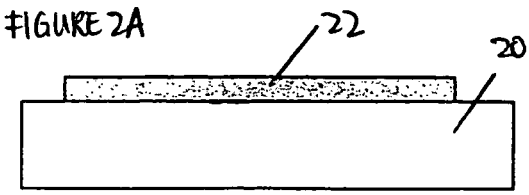
FIGS. 2A-2N show cross-sectional views of fabrication steps of a sensor of a second embodiment of the present invention.
Figure 2G:
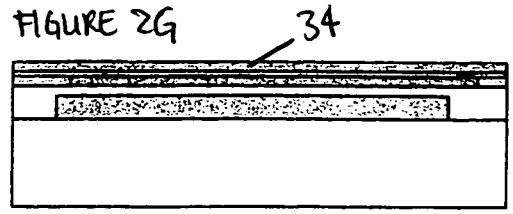
Figure 2B:
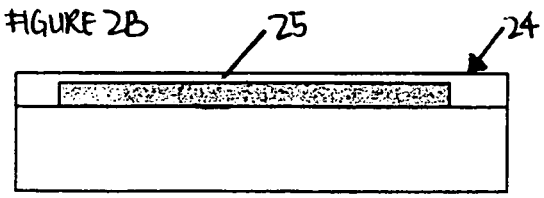
Figure 2H:
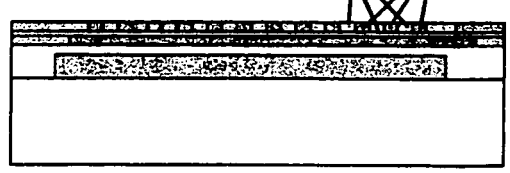
Figure 2C:
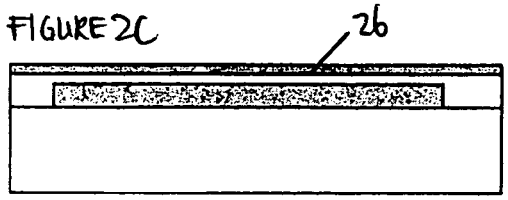
Figure 2I:
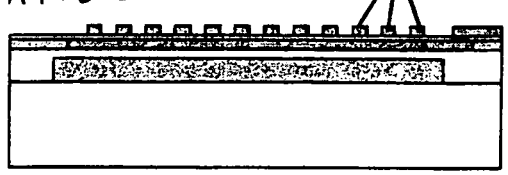
Figure 2D:
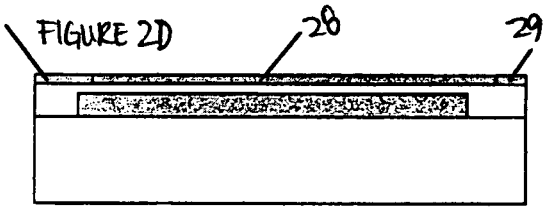
Figure 2J:
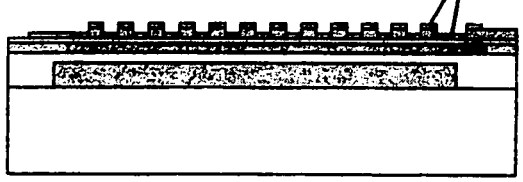
Figure 2E:
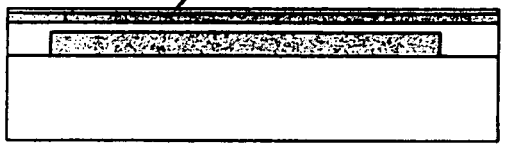
Figure 2K:
Figure 2F:
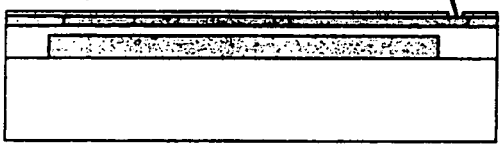
Figure 2L:
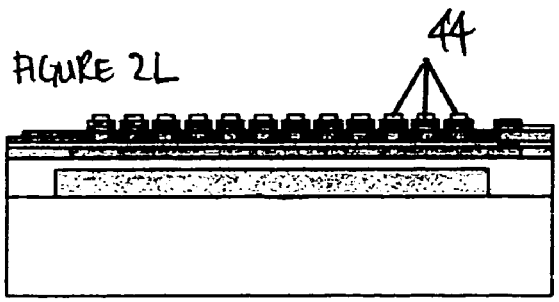
Figure 2M:
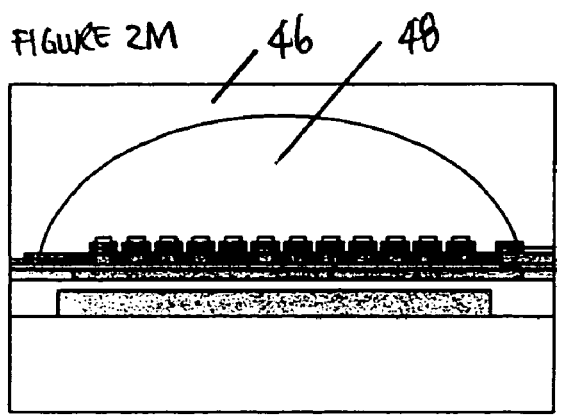
Figure 2N:
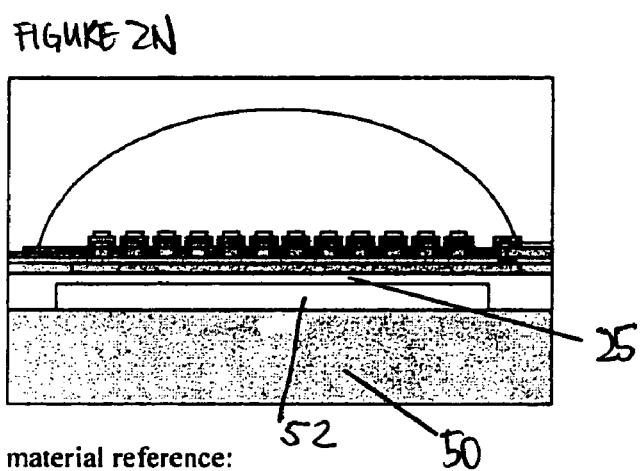
Figure 2N:
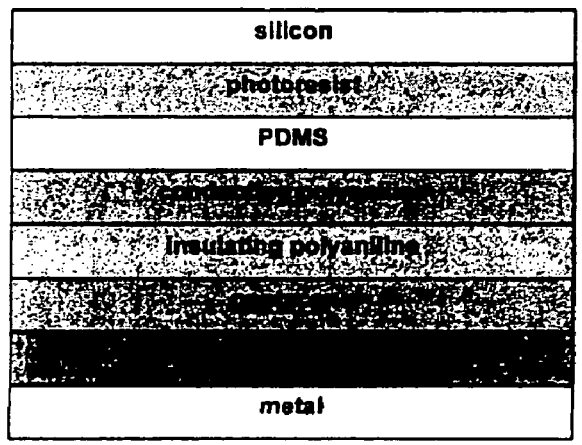

FIGS. 2A-2N illustrate the step by step preferred process of fabricating the sensor of the second embodiment. In FIG. 2A, the process of fabrication begins with a temporary substrate 20, such as a silicon wafer or any other substrate, with a soft lithography mold pattern 22 for fabricating a membrane layer 24 (shown in FIG. 2B). The material of the soft lithography mold pattern 22 may be made of a photoresist, which may be used to function as a sacrificial release layer at a later stage of the fabrication process in order to suspend a membrane 25 (shown in FIG. 2B). Any other suitable mold pattern 22 as the sacrificial layer may also be used.

In FIG. 2B, the membrane layer 24, preferably made of an elastomer, is formed, preferably by spin coating, over the mold 22. Note that the thickness of the membrane 25 over the mold pattern 22 determines compliance of the membrane 25 during sensor operation. The membrane layer 24 may be fabricated from organic polymers such as poly-dimethylsiloxane (PDMS) using soft lithography, or Su-8 negative photoresist using standard microfabrication methods, such as those described by J. Thaysen et al (Phys. D. 35, 2698-2703 (2002)). Other organic or inorganic materials, such as parylene, may also be used.

After the membrane layer 24 is formed, a first layer of conducting polymer 26, such as polyaniline or poly(3,4-ethylenedioxythiophene) (PEDOT), is spin deposited from solution on the membrane layer 24 as shown in FIG. 2C. FIG. 2D shows the first layer of conducting polymer 26 being lithographically patterned to form a plurality of gate electrodes 28. For example, the gate electrodes 28 may be masked and not exposed to radiation while the remainder of the polymer layer 26 is exposed to radiation, such as 240 nm radiation. Note that after the negative lithography process, insulating regions 29 are formed in the exposed regions of the polymer layer 26. These regions 29 are not removed.

FIG. 2E shows a layer of insulating material 30, such as an organic insulating material, being spin deposited on the patterned first layer of conducting polymer 26. The insulating material 30 may comprise a photoresist layer which serves as the gate dielectric for the gate electrodes 28. The insulating material 30 is a planar layer due to the presence of the insulating regions 29 between the gate electrodes 28. FIG. 2F shows the insulating material 30 patterned to define via interconnects 32 to the gate electrodes 28 or any metallic fanout electrodes (not shown in the figure) if desired.

Next, as shown in FIG. 2G, a second layer of conducting polymer 34, such as polyaniline or poly(3,4-ethylenedioxythiophene) (PEDOT), is spin deposited over the insulating layer 30. The second layer of conducting polymer 34 is subsequently lithographically patterned to form a plurality of source/drain electrodes 36 as seen in FIG. 2H. The source/drain electrodes 36 may act as either a source or drain electrode. Specifically, the source/drain electrodes 36 are not exposed to radiation (e.g. by masking the source/drain electrodes 36) while a remainder of the polymer layer 34 is exposed to radiation, for instance to 240 nm radiation. Due to the negative lithography process, the exposed regions in the polymer layer 34 are converted to insulating regions 38. These insulating regions 38 are removed as shown in FIG. 2I. It is noted that the gate electrodes 28 and source/drain electrodes 36 are patterned in such a way to achieve a cross bar arrangement and hence an array of sensors.

Once the source/drain electrodes 36 are formed, an organic semiconductor layer 40, such as pentacene, is deposited by thermal evaporation through a shadow mask formed by the source/drain electrodes 36. This is illustrated in FIG. 2J. Portions of the organic semiconductor layer 40 formed between the source/drain electrodes 36 act as transistor channels while the remaining portions of the layer 40 are formed over the electrodes 36. Pentacene may alternatively be deposited by solution deposition of precursor material followed by photo and thermal conversion to pentacene.

A passivation layer 42 is then vapor deposited to encapsulate any exposed area on the organic semiconductor layer 40, as shown in FIG. 2K. When the organic semiconductor layer 40 comprises pentacene, the passivation layer 42 is preferably an organic polymer, such as parylene. It is known that parylene is a potential encapsulating layer for protecting pentacene channels in thin film transistors during additional processing steps. Parylene is vapor deposited under a vacuum and forms pinhole free conformal coatings and has been shown to have excellent biocompatibility. In this way, bottom gate thin film transistors are formed on the temporary substrate 20.

In order to establish robust and controlled mechanical connections, in particular for use in a cell, metal contact pads 44 and metal fanout electrodes are patterned and deposited on top of the thin film transistor array (i.e. on top of the passivation layer 42) as seen in FIG. 2L. For applications in a biosensor, the metal contact pads 44 may be further chemically functionalized with analyte binding molecules which selectively bind to a desired analyte, such as cells. The metal contact pads 44 are deposited using selective ebeam evaporation or other deposition methods, and may be patterned using ebeam or photolithography. The metal contact pads 44 are located outside of the membrane layer 24, where they are in contact with the source/drain electrodes 36 and the gate electrodes 28 of the sensor array. FIG. 2L shows the completion of the sensor array.

For a biosensor or other chemical analyte sensors, FIG. 2M illustrates an integrated elastomer based microfluidic handling system 46 applied to the completed sensor array of FIG. 2L. The microfluidic handling system 46 may be fabricated from PDMS using methods developed by Quake and his collaborators (Unger M. A. et al. Science 288, 113-116 (2000); Shou H. P. et al. PNAS 96, 11-13 (1999)). A testing volume or testing chamber 48 is located between the sensor array and the microfluidic handling system 46. The analyte fluid is provided into the testing chamber 48 from the microfluidic handling system 46. External electronics (not shown in the figure) are connected to the sensor array for addressing and reading the sensor array.

After the microfluidic handling system 46 is applied, the membrane layer 24 is subsequently suspended and transferred to a glass substrate 50. Specifically, the temporary substrate is removed from the sensor array and the soft lithography mold pattern 22, functioning as a sacrificial release layer, is selectively etched away to form the membrane 25 (as the mechanical resonator) in membrane layer 24. The membrane is suspended over a cavity 52 where the removed sacrificial pattern 22 used to be located. FIG. 2N shows the cross-section of the sensor of the second embodiment of the invention, integrated with the microfluidic handling system 46.

Methods for fabricating all organic integrated thin film transistor circuits are known in the art and several different processes may be used in patterning the source, drain and gate electrodes from conducting polymers as part of the fabrication process disclosed above. For instance, the use of deep ultraviolet (wavelength of approximately 240 nm) lithography for patterning the source, drain and gate electrodes from conducting polymer layers such as polyaniline or poly(3,4-ethylenedioxythiophene) (PEDOT), are known to achieve 1 micron features. The use of I-line (wavelength of approximately 365 nm) lithography for patterning conducting PEDOT is also known to achieve 2.5 micron features.

Conducting polyaniline and PEDOT wires are compatible with the use of commercial photoresists, which are used as lithographically patternable gate dielectric and interconnect insulator. All of these processes are compatible with the use of pentacene as the transistor channel.

Figure 3:
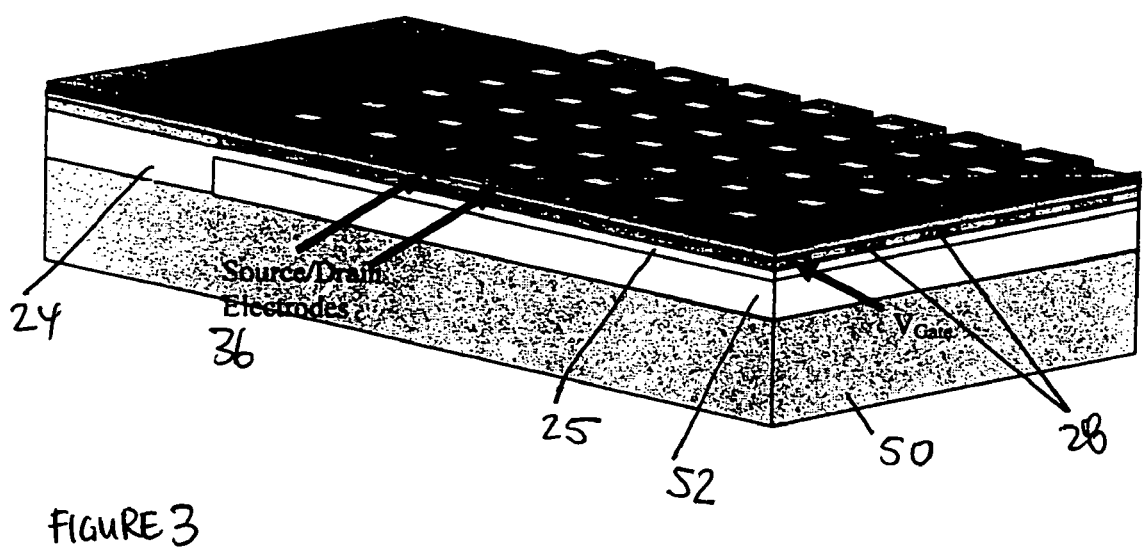
FIG. 3 shows a perspective view of the sensor of the second embodiment.

The conducting polyaniline gate electrodes 28 and conducting polyaniline source/drain electrodes 36 form a cross bar arrangement depicted in FIG. 3. The thin film transistors are located at intersections of each of the gate electrodes 28 with two of the source/drain electrodes 36, where the pentacene transistor channel regions are located between the two directly adjacent source/drain electrodes 36.

Similar to the first embodiment, during operation of the sensor, applying an adequate bias voltage ($V_{gate}$) on any one of the gate electrodes 28 will accumulate charge carriers in the organic semiconductor layer 40 (i.e. in a selected thin film transistor channel). Due to the cross bar arrangement as shown in FIG. 3, only portions of the organic semiconductor layer 40 that are directly above the biased gate electrode (i.e. the selected thin film transistor channel directly aligned with the said biased gate electrode) accumulate charge carriers.

Figure 4:
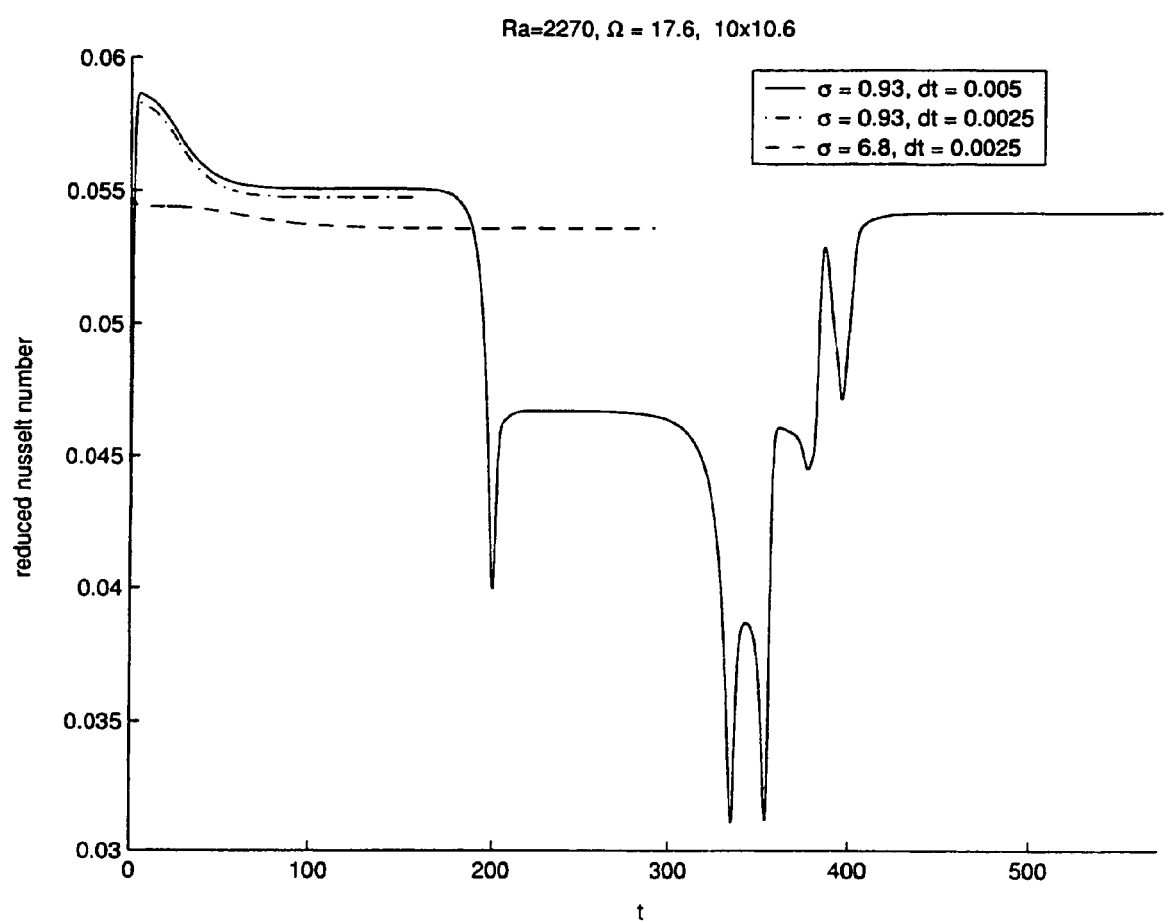
FIG. 4 shows a graph of the rate of change of the reduced nusselt number versus time of the sensor of the second embodiment.

This leaves the rest of the organic semiconductor layer 40 (i.e. the rest of the thin film transistor channels) non-conducting. FIG. 4 shows a graph of the rate of change of the reduced nusselt number versus time of the sensor of the second embodiment.

Therefore, by utilizing the piezoresistive effect in the organic semiconductor layer 40 together with the cross bar arrangement of the source/drain electrodes 36 and the gate electrodes 28, the membrane 25 is divided into a dense array of individually addressable sensors. Any strain or force on the membrane 25 is then measured by measuring a change in resistance or current between a pair of source/drain electrodes 36 that is dominated by the single 1 micron by 1 micron patch of organic semiconductor layer 40, that has been addressed by the biased gate electrode. As a result, the sensor of the second embodiment of the present invention is able to improve spatial resolution down to 1 micron. It is believed that the sensor can be used to probe the structural state of the cell cytoskeleton more sensitively than the prior art sensors. Specifically, an analyte fluid containing a desired analyte such as cells is provided into the testing chamber 48. Cells bind to the resonator, such as the membrane 25, causing the resonator to experience a force or strain which is detected due to a change in the current between selected adjacent source/drain electrodes 36.

In addition, connection of external electronics to the sensor array will enable continuous, real time measurement with 1 millisecond resolution for a single force and strain sensor, and 1 second resolution for the entire sensor array. Furthermore, the electronic readout will ease the requirement for optical access, enabling integration of complex microfluidics and force actuators. The sensor array described above may be used in other types of sensors such as pressure sensors, accelerometers, etc.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention. All of the publications, patent applications and patents cited in this specification are incorporated herein by reference in their entirety.

What is claimed is:

1. A MEMS system comprising:
   a micromechanical resonator; and
   a piezoresistive sensing element comprising an organic semiconductor.

2. The system of claim 1, wherein the organic semiconductor comprises a channel of a transistor and the system comprises a sensor.

3. The system of claim 1, wherein the micromechanical resonator comprises a polymer material.

4. The system of claim 1, wherein the organic semiconductor comprises pentacene.

5. The system of claim 1, wherein the resonator is a torsional resonator or a force sensing beam or a cantilever or a membrane.

6. The system of claim 2, wherein the transistor is an organic thin film transistor and the sensor comprises a biosensor.

7. The system of claim 6, wherein the transistor consists essentially of organic polymers.

8. A micromechanical sensor array comprising:
   a micromechanical resonator; and
   at least one transistor piezoresistive sensing element comprising an organic semiconductor channel.

9. The micromechanical sensor array of claim 8, wherein each transistor piezoresistive sensing element further comprises:
   at least one gate electrode; and
   a plurality of source and drain electrodes;
   wherein the plurality of source and drain electrodes and the gate electrodes are arranged on the micromechanical resonator to form a plurality of thin film transistor piezoresistive sensing elements, each comprising the organic semiconductor channel.

10. The sensor array of claim 8, further comprising a passivation layer encapsulating any exposed area on the organic semiconductor.

11. The sensor array of claim 8, further comprising external electronics connected to the sensor array for addressing and reading the sensor array.

12. The sensor array of claim 8, further comprising a microfluidic handling system.

13. The sensor array of claim 9, wherein the plurality of source and drain electrodes and the gate electrodes are in a cross bar arrangement.

14. The micromechanical sensor array of claim 9, wherein the micromechanical resonator is a suspended membrane over a substrate.

15. The sensor array of claim 9, wherein the gate, source and drain of each of the thin film transistors are accessible by at least one metal contact.

16. The sensor array of claim 9, wherein the organic semiconductor comprises pentacene and the gate electrodes and the plurality of source and drain electrodes comprise polyaniline or poly(3,4-ethylenedioxythiophene).

17. A method of using a sensor, comprising:
   exposing a sensor comprising a micromechanical resonator and a piezoresistive sensing element comprising an organic semiconductor to a stimulus or an analyte which causes mechanical movement of the resonator; and
   measuring a change in current through the organic semiconductor due to the mechanical movement of the resonator.

18. The method of claim 17, wherein sensor comprises a biofunctionalized biosensor and the change in current through the organic semiconductor comprises a change in current through an organic semiconductor channel of a thin film transistor which indicates a presence or absence of binding between the analyte and the sensor.

* * * * *